United States Patent [19]

Minaskanian et al.

[11] Patent Number: 5,470,848

[45] Date of Patent: * Nov. 28, 1995

[54] PENETRATION ENHANCERS FOR TRANSDERMAL DELIVERY OF SYSTEMIC AGENTS

[76] Inventors: Gevork Minaskanian, 8 Havenwood, Irvine, Calif. 92714; James V. Peck, 2524 Bowdoin Pl., Costa Mesa, Calif. 92626

[*] Notice: The portion of the term of this patent subsequent to Jun. 2, 2009, has been disclaimed.

[21] Appl. No.: 139,684

[22] Filed: Oct. 22, 1993

Related U.S. Application Data

[62] Division of Ser. No. 989,434, Dec. 11, 1992, abandoned, which is a division of Ser. No. 611,613, Nov. 13, 1990, Pat. No. 5,234,959, which is a continuation of Ser. No. 199,801, Jun. 20, 1988, Pat. No. 4,996,199, which is a continuation-in-part of Ser. No. 179,144, Apr. 8, 1988, abandoned.

[51] Int. Cl.$^6$ .............. A61K 31/56; A61K 31/445; A61K 31/40; A61K 31/04
[52] U.S. Cl. .............. 514/182; 514/327; 514/424; 514/426; 514/742; 514/947
[58] Field of Search ................... 514/424, 947, 514/182, 327, 742, 426

[56] References Cited

U.S. PATENT DOCUMENTS

| | | | |
|---|---|---|---|
| 4,177,278 | 12/1979 | Bossert et al. | 424/266 |
| 4,808,414 | 2/1989 | Peck et al. | 424/449 |
| 4,837,026 | 6/1989 | Rajakhyaksha | 424/449 |
| 4,882,359 | 11/1989 | Nakagawa et al. | 514/947 |
| 4,946,870 | 8/1990 | Partain, III et al. | 514/777 |
| 4,960,771 | 10/1990 | Rajakhyaksha | 514/228.8 |
| 5,118,676 | 6/1992 | Minaskanian et al. | 514/183 |
| 5,118,692 | 6/1992 | Peck | 514/317 |

FOREIGN PATENT DOCUMENTS

| | | |
|---|---|---|
| 241050 | 10/1987 | European Pat. Off. |
| WO88/04938 | 7/1988 | WIPO |

*Primary Examiner*—Raymond Henley, III
*Attorney, Agent, or Firm*—Sterne, Kessler, Goldstein & Fox

[57] ABSTRACT

This invention relates to a method for administering systemically active agents through the skin or mucosal membranes of humans and animals and into the bloodstream in a transdermal device or formulation comprising topically administrating with said systemic agent an effective amount of a membrane penetration enhancer having the structural formula

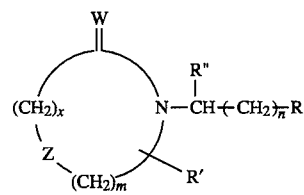

or the pharmaceutically acceptable salt thereof wherein W represents oxygen, sulfur or two hydrogen radicals; Z represents —$CH_2$—; R represents alkyl optionally substituted with one to three double or triple bonds, —SR''', —OR''', —NHR''', or —$COOR_1$; R''' represents alkyl, alkylthioalkyl, alkoxyalkyl, amino alkyl, optionally substituted with a phenyl, or benzoyl; R' represents hydrogen, alkyl, alkoxy, acyloxy, alkylthio, hydroxy or —$(CH_2)_y COOR_1$; R'' represents hydrogen or —$(CH_2)_y COOR_1$; $R_1$, in each instance, independently represents hydrogen or lower alkyl; y, in each instance, is between zero and 3, inclusive; m is between one and 3, inclusive; n is between one and 24, inclusive; and x is zero or one, inclusive;

with the provisos that when R'' is hydrogen, then W is two hydrogen radicals and R' is not hydrogen; and when R' is hydrogen, then R'' is not hydrogen. It has been found that the penetration enhancers are sufficient to carry physiologically active agents through body membranes and into the bloodstream.

7 Claims, No Drawings

PENETRATION ENHANCERS FOR TRANSDERMAL DELIVERY OF SYSTEMIC AGENTS

REFERENCE TO EARLIER FILED APPLICATIONS

This application is a division of application Ser. No. 07/989,434, filed Dec. 11, 1992, now abandoned which is a division of application Ser. No. 07/611,613, filed Nov. 13, 1990 now U.S. Pat. No. 5,234,959, which is a continuation of application Ser. No. 07/199,801, filed Jun. 20, 1988 now U.S. Pat. No. 4,996,199 which is a continuation-in-part of application Ser. No. 07/179,144, filed Apr. 8, 1988, now abandoned.

BACKGROUND OF THE INVENTION 1. Field of the Invention

The invention generally relates to an improved method of drug delivery. More particularly, the invention relates to an improved membrane penetration enhancer for use in the transdermal delivery of systemically active drugs to humans and animals.

2. Background of the Prior Art

For some years, pharmaceutical researchers have sought an effective means of introducing drugs into the bloodstream by applying them to unbroken skin. Among other advantages, such administration can provide a comfortable, convenient, and safe way of giving many drugs now taken orally or infused into veins or injected intramuscularly.

Using skin as the portal for drug entry offers unique potential, because transdermal delivery permits close control over drug adsorption. For example, it avoids factors that can cause unpredictable absorption from the gastrointestinal tract, including: changes in acidity, motility, and food content. It also avoids initial metabolism of the drug by the liver. Thus, controlled drug entry through skin can achieve a high degree of control over blood concentrations of drug.

Close control over drug concentrations in blood can translate readily into safer and more comfortable treatment. When a drug's adverse effects occur at higher concentrations than its beneficial ones, rate control can maintain the concentrations that evoke only—or principally—the drug's desired actions. This ability to lessen undesired drug actions. This ability to lessen undesired drug actions can greatly reduce the toxicity hazards that now restrict or prevent the use of many valuable agents.

Transdermal delivery particularly benefits patients with chronic disease. Many such patients have difficulty following regimens requiring several doses daily of medications that repeatedly cause unpleasant symptoms. They find the same drugs much more acceptable when administered in transdermal systems that require application infrequently— in some cases, only once or twice weekly—and that reduce adverse effects.

Transdermal delivery is feasible for drugs effective in amounts that can pass through the skin area and that are substantially free of localized irritating or allergic effects. While these limitations may exclude some agents, many other remain eligible for transdermal delivery. Moreover, their numbers will expand as pharmaceutical agents of greater potency are developed. Particularly suitable for transdermal delivery are potent drugs with only a narrow spread between their toxic and safe blood concentrations, those having gastrointestinal absorption problems, or those requiring frequent dosing in oral or injectable form.

Transdermal therapy permits much wider use of natural substances such as hormones. Often the survival times of these substances in the body are so short that they would have to be taken many times daily in ordinary dosage forms. Continuous transdermal delivery provides a practical way of giving them, and one that can mimic the body's own patterns of secretion.

At present, controlled transdermal therapy appears feasible for many drugs used for a wide variety of ailments including, but not limited to, circulatory problems, hormone deficiency, respiratory ailments, and pain relief.

Percutaneous administration can have the advantage of permitting continuous administration of drug to the circulation over a prolonged period of time to obtain a uniform delivery rate and blood level of drug. Commencement and termination of drug therapy are initiated by the application and removal of the dosing devices from the skin. Uncertainties of administration through the gastrointestinal tract and the inconveniences of administration by injection are eliminated. Since a high concentration of drug never enters the body, problems of pulse entry are overcome and metabolic half-life is not a factor of controlling importance.

U.S. Pat. Nos. 3,989,815; 3,989,816; 3,991,203; 4,122,170; 4,316,893; 4,415,563; 4,423,040; 4,424,210; and 4,444,762 generally describe a method for enhancing the topical (as contrasted to the systemic) administration of physiologically active agents by combining such an agent with an effective amount of a penetration enhancer and applying the combination topically to humans or animals, in the form of creams, lotions, gels, etc.

Penetration enhancers for enhancing systemic administration of therapeutic agents transdermally are cited in U.S. Pat. Nos. 4,405,616; 4,462,075; 4,031,894, 3,996,934; and 3,921,636.

SUMMARY OF THE INVENTION

It has been discovered that the penetration enhancers previously disclosed in U.S. patent application Ser. No. 179,144, filed on Apr. 8, 1988, to enhance topical delivery of physiologically active agents also enhance the transdermal delivery of systemically active agents through the skin or other body membranes of humans and animals directly into the bloodstream.

The invention therefore provides a method for topically administering systemically active agents through the skin or mucosal membranes of humans and animals, utilizing a transdermal device or formulation, wherein the improvement in said method comprises topically administering with said systemic agent an effective amount of a membrane penetration enhancer having the general formulae

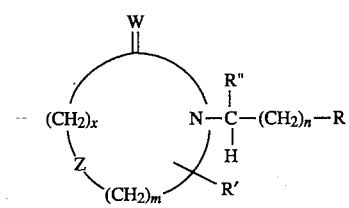

wherein W represents oxygen, sulfur, or two hydrogen radicals;

wherein Z represents oxygen, sulfur, or —$CH_2$—;

wherein R represents alkyl optionally substituted with one to three double or triple bonds, —SR''', —OR''', —NHR''', —CH$_3$, or COOR$_1$, and wherein R$_1$ represents hydrogen or lower alkyl;

wherein R''' represents alkyl, alkylthioalkyl, alkoxyalkyl, substituted aminoalkyl, optionally substituted with a phenyl, benzoyl or heterocyclic group;

wherein R' represents hydrogen, alkyl, alkoxy, acyloxy, alkylthio, hydroxy, —(CH2)$_y$COOR$_1$ and with y being between zero and 3, inclusive;

and wherein R'' represents hydrogen or —(CH 2)$_y$COOR$_1$ such that when R'' is hydrogen, then W is two hydrogen radicals and R' is not hydrogen; and when R' is hydrogen, then R'' is not hydrogen;

and wherein m is between one and 5, preferably 2, 3, or 4, while n is between 1 and 24, preferably between 5 and 12, and x is zero or 1, inclusive.

In an alternative embodiment, the novel penetration enhancers include compounds represented by the general formula:

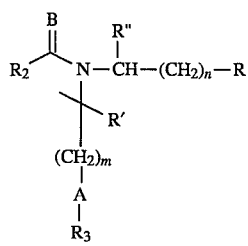

wherein B represents oxygen, sulfur, or two hydrogen radicals;

wherein A represents oxygen, sulfur, or —(CH$_2$)—; wherein R, R$_2$ and R$_3$ independently represent alkyl optionally substituted with 1 to 3 double or triple bonds, —SR''', —OR''', —NHR''', —CH$_3$, or COOR$_1$;

wherein R''' represents hydrogen, alkyl, alkylthioalkyl, alkoxyalkyl, substituted aminoalkyl, optionally substituted with a phenyl, benzoyl, or heterocyclic group;

wherein R' represents hydrogen, alkyl, alkoxy, acyloxy, alkylthio, hydroxy, or —(CH2)$_y$COOR$_1$;

wherein R'' represents hydrogen, or —(CH2)$_y$COOR$_1$;

wherein R$_1$ represents a hydrogen or lower alky radical and y is between zero 0 and 3, inclusive.

wherein m is between zero and 5, preferably 1 or 2; while n is between 1 and 24, preferably between 5 and 12, inclusive;

And in yet another embodiment the compound is represented by the formula:

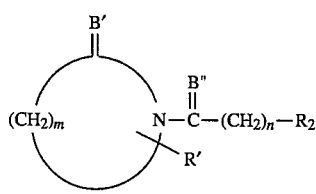

wherein R$_2$ is COOR$_1$ or an alkyl radical, optionally substituted with between 1 and 3 double or triple bonds;

wherein R' is a hydrogen radical, alkyl, alkoxy, acyloxy, alkylthio, hydroxy, or —(CH$_2$)$_y$COOR$_1$;

wherein B' represents oxygen, sulfur, or two hydrogen radicals;

wherein B'' represents oxygen, sulfur, or two hydrogen radicals such that when B'' is not hydrogen, B' is two hydrogen radicals, and R$_2$ is alkyl, then R' is —(CH$_2$)$_y$COOR$_1$ where y cannot be zero;

wherein y is between zero and three, inclusive, and R$_1$ represents a lower alkyl or hydrogen radical;

and wherein m is between 3 and 6, preferably 3, 4 or 5 while n is between 1 and 24, preferably between 5 and 12, inclusive;

and wherein y is between zero and three, inclusive, and R$_1$ represents a lower alkyl or hydrogen radical.

DETAILED DESCRIPTION OF INVENTION

Novel transdermal penetration enhancers useful in the method of the present invention include carboxylic acid derivatives and their salts, which are compounds represented by the general formulae:

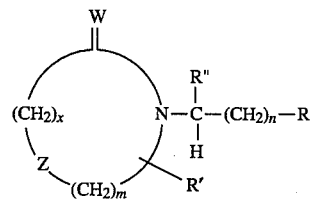

wherein W represents oxygen, sulfur, or two hydrogen radicals;

wherein Z represents oxygen, sulfur, or —CH$_2$—;

wherein R represents alkyl optionally substituted with one to three double or triple bonds, —SR''', —OR''', —NHR''', —CH$_3$, or COOR$_1$, and wherein R$_1$ represents hydrogen or lower alkyl;

and wherein R''' represents alkyl, alkylthioalkyl, alkoxyalkyl, substituted aminoalkyl, optionally substituted with a phenyl, benzoyl or heterocyclic group;

wherein R' represents hydrogen, alkyl, alkoxy, acyloxy, alkylthio, hydroxy, —(CH$_2$)$_y$COOR$_1$ and with y being between zero and 3, inclusive;

wherein R'' represents hydrogen or —(CH2)$_y$COOR$_1$ such that when R'' is hydrogen, then W is two hydrogen radicals and R' is not hydrogen; and when R' is hydrogen, then R'' is not hydrogen;

and wherein m is between one and 5, preferably 2, 3, or 4 while n is between 1 and 24, preferably between 5 and 12, inclusive, and x is zero or 1, inclusive.

In an alternative embodiment, the compounds useful as penetration enhancers include those represented by the general formula:

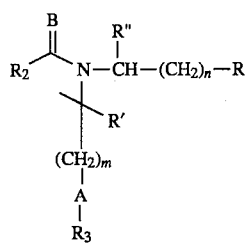

wherein B represents oxygen, sulfur, or two hydrogen radicals;

wherein A represents oxygen, sulfur or —(CH$_2$)—;

wherein R, R$_2$ and R$_3$ independently represent alkyl optionally substituted with 1 to 3 double or triple bonds, —SR''', —OR''', —NHR''', —CH$_3$, or COOR$_1$;

wherein R''' represents hydrogen, alkyl, alkylthioalkyl, alkoxyalkyl, substituted aminoalkyl, optionally substituted with a phenyl, benzoyl, or heterocyclic group;

wherein R' represents hydrogen, alkyl, alkoxy, acyloxy, alkylthio, hydroxy, or —(CH2)$_y$COOR$_1$;

wherein R" represents hydrogen or —(CH2)$_y$COOR$_1$;

wherein m is between zero and 5, preferably 1 or 2; while n is between 1 and 24, preferably between 5 and 12, inclusive;

and wherein R$_1$ represents a hydrogen or lower alkyl radical and y is between zero and 3, inclusive.

And in yet another embodiment the compound is represented by the formula:

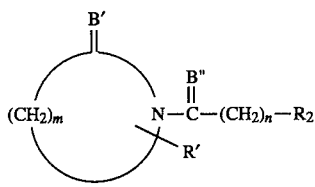

wherein R$_2$ is COOR$_1$ or an alkyl radical, optionally substituted with between 1 and 3 double or triple bonds;

wherein R' is a hydrogen radical, alkyl, alkoxy, acyloxy, alkylthio, hydroxy, or —(CH$_2$)$_y$COOR$_1$;

wherein B' represents oxygen, sulfur, or two hydrogen radicals;

wherein B" represents oxygen, sulfur, or two hydrogen radicals such that when B" is not hydrogen, B' is two hydrogen radicals, and R$_2$ is alkyl, then R' is —(CH$_2$)$_y$COOR$_1$ where y is not zero;

wherein y is between zero and three, inclusive, and R$_1$ represents a lower alkyl or hydrogen radical.

and wherein m is between 3 and 6, preferably 3,4,or 5, while n is between 1 and 24, preferably between 5 and 12, inclusive;

These novel transdermal penetration-enhancing additives may be made by the methods illustrated in the Examples below. Typical examples of compounds represented by the above general formulae include:

1-N-dodecyl-2-pyrrolidone-5-carboxylic acid
1-N-butyl-2-pyrrolidone-5-carboxylic acid
1-N-pentyl-2-pyrrolidone-5-carboxylic acid
1-N-hexyl-2-pyrrolidone-5-carboxylic acid
1-N-octyl-2-pyrrolidone-5-carboxylic acid
1-N-nonyl-2-pyrrolidone-5-carboxylic acid
1-N-decyl-2-pyrrolidone-5-carboxylic acid
1-N-tetradecyl-2-pyrrolidone-5-carboxylic acid
1-N-hexadecyl-2-pyrrolidone-5-carboxylic acid
1-N-heptyl-2-pyrrolidone-5-carboxylic acid
1-N-dodecyl-2-piperidone-6-carboxylic acid
1-N-butyl-2-piperidone-6-carboxylic acid
1-N-pentyl-2-piperidone-6-carboxylic acid
1-N-hexyl-2-piperidone-6-carboxylic acid
1-N-octyl-2-piperidone-6-carboxylic acid
1-N-nonyl-2-piperidone-6-carboxylic acid
1-N-decyl-2-piperidone-6-carboxylic acid
1-N-tetradecyl-2-piperidone-6-carboxylic acid
1-N-hexadecyl-2-piperidone-6-carboxylic acid
1-N-heptyl-2-piperidone-6-carboxylic acid
1-(2-(n-dodecylthio)ethyl)-2-pyrrolidone-5-carboxylic acid
1-(2-(n-butylthio)ethyl)-2-pyrrolidone-5-carboxylic acid
1-(2-(n-pentylthio)ethyl)-2-pyrrolidone-5-carboxylic acid
1-(2-(n-hexylthio)ethyl)-2-pyrrolidone-5-carboxylic acid
1-(2-(n-octylthio)ethyl)-2-pyrrolidone-5-carboxylic acid
1-(2-(n-nonylthio)ethyl) -2-pyrrolidone-5-carboxylic acid
1-(2-(n-decylthio)ethyl) -2-pyrrolidone-5-carboxylic acid
1-(2-(n-tetradecylthio)ethyl)-2-pyrrolidone-5-carboxylic acid
1-(2-(n-hexadecylthio)ethyl)-2-pyrrolidone-5-carboxylic acid
1-(2-(n-heptylthio)ethyl)-2-pyrrolidone-5-carboxylic acid
1-(2-(n-dodecylthio)ethyl)-piperidine-3-carboxylic acid
1-(2-(n-butylthio)ethyl)-piperidine-3-carboxylic acid
1-(2-(n-pentylthio)ethyl)-piperidine-3-carboxylic acid
1-(2-(n-hexylthio)ethyl)-piperidine-3-carboxylic acid
1-(2-(n-octylthio)ethyl)-piperidine-3-carboxylic acid
1-(2-(n-nonylthio)ethyl)-piperidine-3-carboxylic acid
1-(2-(n-decylthio)ethyl)-piperidine-3-carboxylic acid
1-(2-(n-tetradecylthio)ethyl)-piperidine-3-carboxylic acid
1-(2-(n-hexadecylthio)ethyl)-piperidine-3-carboxylic acid
1-(2-(n-heptylthio)ethyl)-piperidine-3-carboxylic acid
2-dodecyl,2-N-(2-pyrrolidone)-acetic acid
2-butyl,2-N-(2-pyrrolidone)-acetic acid
2-pentyl,2-N-(2-pyrrolidone)-acetic acid
2-hexyl,2-N-(2-pyrrolidone)-acetic acid
2-octyl,2-N-(2-pyrrolidone)-acetic acid
2-nonyl,2-N-(2-pyrrolidone)-acetic acid
2-decyl,2-N-(2-pyrrolidone)-acetic acid
2-tetradecyl,2-N-(2-pyrrolidone)-acetic acid
2-hexadecyl,2-N-(2-pyrrolidone)-acetic acid
2-heptyl,2-N-(2-pyrrolidone)-acetic acid
2-dodecyl,2-N-(2-piperidone)-acetic acid
2-dodecyl,2-N-(azacycloheptane-2-one)-acetic acid
2-butyl,2-N-(azacycloheptane-2-one)-acetic acid
2-pentyl,2-N-(azacycloheptane-2-one)-acetic acid
2-hexyl,2-N-(azacycloheptane-2-one)-acetic acid
2-octyl,2-N-(azacycloheptane-2-one)-acetic acid
2-nonyl,2-N-(azacycloheptane-2-one)-acetic acid
2-decyl,2-N-(azacycloheptane-2-one)-acetic acid
2-tetradecyl,2-N-(azacycloheptane-2-one)-acetic acid
2-hexadecyl,2-N-(azacycloheptane-2-one)-acetic acid
2-heptyl,2-N-(azacycloheptane-2-one)-acetic acid
6-(N-pyrrolidine)-hexanoic acid
8-(N-pyrrolidine)-octanoic acid
10-(N-pyrrolidine)-decanoic acid
12-(N-pyrrolidine)-dodecanoic acid
12-diethylaminododecanoic acid
10-diethylaminodecanoic acid
6-diethylaminohexanoic acid
8-diethylaminooctanoic acid 2-(N-morpholine)-2-dodecylacetic acid
2-(N-morpholine)-2-decylacetic acid
2-(N-morpholine)-2-octylacetic acid
2-(N-morpholine)-2-hexylacetic acid
2-(N-morpholine)-2-butylacetic acid It has also been found that the penetration enhancers herein also themselves possess antiviral activity and can be used alone to combat viral infections.

Typical systemically active agents which may be delivered transdermally are therapeutic agents which are sufficiently potent such that they can be delivered through the skin or other membrane to the bloodstream in sufficient quantities to produce the desired therapeutic effect. In general, this includes therapeutic agents in all of the major therapeutic areas including, but not limited to, anti-infectives, such as antibiotics and antiviral agents, analgesics and analgesic combinations, anorexics, antihelmintics, antiarthritics, antiasthma agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, ant ipyretics, antispasmodics, including gastrointestinal and urinary; anticholinergics, sympathomimetics, xanthine derivatives, cardiovascular preparations including calcium channel blockers, betablockers, antiarrhythmics, antihypertensives, diuretics, vasodialators including general, coronary, peripheral and cerebral; central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

Dosage forms for application to the skin or other membranes of humans and animals include creams, lotions, gels, ointments, suppositories, sprays, aerosols, buccal and sublingual tablets and any one of a variety of transdermal devices for use in the continuous administration of systemically active drugs by absorption through the skin, oral mucosa or other membranes, see, for example, one or more of U.S. Pat. Nos. 3,598,122; 3,598,123; 3,731,683; 3,742, 951; 3,814,097; 3,921,636; 3,972,995; 3,993,072; 3,993, 073, 3,996,934; 4,031,894; 4,060,084;4,069,307; 4,201,211; 4,230,105; 4,292,299 and 4,292,303. U.S. Pat. No. 4,077, 407 and the foregoing patents also disclose a variety of specific systemically active agents which may also be useful in transdermal delivery, which disclosures are hereby incorporated herein by this reference.

Typical inert carriers which may be included in the foregoing dosage forms include conventional formulating materials, such as, for example, water, isopropyl alcohol, gaseous fluorocarbons, ethyl alcohol, polyvinyl pyrrolidone, propylene glycol, fragrances, gel-producing materials such as "Carbopol", stearyl alcohol, stearic acid, spermaceti, sorbitan monooleate, "Polysorbates", "Tweens", sorbital, methylcellulose, etc.

Systemically active agents are used in amounts calculated to achieve and maintain therapeutic blood levels in a human or animal over the period of time desired. These amounts vary with the potency of each systemically active substance, the amount required for the desired therapeutic or other effect, the rate of elimination or breakdown of the substance by the body once it has entered the bloodstream and the amount of penetration-enhancer in the formulation. In accordance with conventional prudent formulating practices, a dosage near the lower end of the useful range of a particular agent is usually employed initially and the dosage increased or decreased as indicated from the observed response, as in the routine procedure of the physician.

The amount of penetration enhancer which may be used in the invention varies from about 1 to 100 percent although adequate enhancement of penetration is generally found to occur in the range of about 1 to 100 percent although adequate enhancement of penetration is generally found to occur in the range of about 1 to about 10 percent by weight of the formulation to be delivered. The penetration-enhancer disclosed herein may be used in combination with the active agent or may be used separately as a pretreatment of the skin or other body membrane though which the systemically-active agent is intended to be delivered.

The invention is further illustrated by the following examples which are illustrative of a specific mode of practicing the invention and is not intended as limiting the scope of the appended claims.

EXAMPLE 1

A composition, in the form of a gel, suitable for transdermal delivery of haloperidol, an antidyskinetic or antipsychotic drug, is prepared by mixing the following components in the given concentrations.

| Component | Weight % |
| --- | --- |
| Haloperidol | 1–5. |
| N-dodecyl-2-pyrrolidone-5-carboxylic acid | 1–10 |
| Carbopol 934 P (Available from B. F. Goodrich) | 0.5–2 |
| Neutralizing Agent (NaOH) | q.s. |
| Tween-20 (Available from Atlas Chemical, a Div. of I.C.I.) | 1–10 |
| Preservative (Sorbic Acid) | q.s. |
| Antioxidant (Ascorbic Acid) | q.s. |
| Chelating Agent (Disodium salt of ethylenediaminetetraacetic acid) | q.s. |
| Deionized Water | q.s. to 100 |

This composition is topically applied to the skin of a human subject and after the passage of a suitable period of time haloperidol is found in the bloodstream of said subject.

EXAMPLE 2

When an amine, e.g., triethylamine or triethanolamine, is substituted for NaOH the results are substantially similar, i.e., a topical composition suitable for transdermally delivering haloperidol to the bloodstream is obtained.

EXAMPLE 3

When potassium sorbate, or a lower alkyl paraben, e.g., methyl, ethyl, propyl, or butyl paraben are substituted for the preservative of the composition of Example 1, the results are substantially similar, i.e., a topical composition suitable for the transdermal delivery of haloperidol to the bloodstream is obtained.

EXAMPLE 4

When ascorbyl palmitate, Vitamin E, thioglycerol, thioglycolic acid, sodium formaldehyde sulfoxylate, BHA, BHT, propyl gallate or sodium metabisulfite are substituted for the antioxidant of the composition formulated in Example 1, the results are substantially similar in that a topical composition suitable for transdermally delivering haloperidol to the bloodstream is obtained.

EXAMPLE 5

The composition of Example 1 is prepared in the form of a sodium alginate gel by mixing the following components in the following given concentrations:

| Component | Weight % |
| --- | --- |
| Haloperidol | 1–5 |
| N-dodecyl-2-pyrrolidone-5-carboxylic acid | 1–10 |
| Sodium Alginate | 0.5–5 |
| Calcium Salts | q.s. |
| Tween-20 | 1–10 |
| Preservative* | q.s. |
| Antioxidant** | q.s. |
| Chelating Agent*** | q.s. |
| Deionized Water | to 100 |

*Suitable preservatives are those used in Example 3 as well as sorbic acid.
**Suitable antioxidants are those used in Example 4 including ascorbic acid.

***The chelating agent is the disodium salt of ethylenediaminetetraacetic acid.

This composition when applied topically is found to transdermally deliver haloperidol to the bloodstream of a subject.

EXAMPLE 6

The composition of Example 1 is prepared in the form of a hydrophilic cream by mixing the following components.

| Component | Weight % |
| --- | --- |
| Oil Phase | |
| Cetyl Alcohol | 5–15 |
| Stearyl Alcohol | 1–5 |
| N-dodecyl-2-pyrrolidone-5-carboxylic acid | 0.5–10 |
| Glycerol Monostearate | 2–7 |
| Water Phase | |
| Sodium Laurylsulfate | 0.1 |
| Solvent* | 2–20 |
| Tween-20 | 1–5 |
| Water | q.s. to 100 |

*Suitable solvents are propylene glycol, glycerin, alcohols, for example, ethyl alcohol, isopropyl alcohol, etc., and polyethylene glycols.

The oil phase and the water phase is made up separately, and then agitated to form an emulsion. (When, as in Example 8, the active ingredient is other than haloperidol, depending on its lipophilicity, it will be distributed in the oil or water phase.) This hydrophilic cream, when applied topically to the skin of a human, is found to transdermally delivery haloperidol into the bloodstream.

EXAMPLE 7

The composition of the instant invention may also be delivered by use of a polymeric matrix. For example, a solid polymer such as cellulose triacetate, polyvinyl acetate, terpolymers and copolymers of polyvinyl alcohol and polyvinyl acetate, and silicon elastomers is imbibed with a liquid having the following components in the given concentrations.

| Component | Weight % |
| --- | --- |
| Polymer | 5–40 |
| Haloperidol | q.s. |
| N-dodecyl-2-pyrrolidone-5-carboxylic acid | 0.5–80 |
| Solvent* | 5–90 |
| Surfactant** | 1–10 |
| Preservative*** | q.s. |
| Antioxidant**** | q.s |

*Solvents may be the solvents used in Example 6 above.
**The Surfactant may be Tween-20, glycerol monostearate or sodium laurylsulfate, etc.
***The preservative may be any of the preservatives used in Example 3 above.
****The antioxidants may be any of those used in Example 4 above.

When solid matrix, containing the active ingredients formulated above, is contacted with the skin of a human subject, after a period of time the active agent is found in the bloodstream of said subject.

EXAMPLE 8

Examples 1 to 7 are repeated except that the following active ingredients in the given concentrations are substituted for haloperidol:

| Active Ingredient | Weight % |
| --- | --- |
| Isosorbide Dinitrate | 5–15 |
| Nitroglycerin | 1–5 |
| Estradiol | 1–5 |
| Clonidine | 0.5–3 |
| Propranolol | 1–5 |
| Indomethacin | 5–15 |
| Nifedipine | 1–5 |
| Nicardipine | 1–5 |
| Diclofenac | 5–15 |
| Metaproterenol | 1–5 |

Similar results are obtained in that the active ingredient is transdermally delivered to the bloodstream of an animal.

EXAMPLE 9

Examples 1 to 8 are repeated except that the compounds exemplified on pages 9–12 (except for N-dodecyl-2-pyrrolidone- 5-carboxylic acid) are substituted for N-dodecyl-2-pyrrolidone-5-carboxylic acid. Similar results are obtained in that the active ingredients are transdermally delivered to the bloodstream of an animal. 1-N-dodecyl-2-pyrrolidone-5-carboxylic acid, 2-pentyl-2 -oxo-1-pyrrolidineacetic acid, 2-dodecyl-2-oxo-1-pyrrolidineacetic acid, and 1-azacycloheptan-2-one)-2-dodecylacetic acid are expecially suitable for substitution for N-dodecyl-2-pyrrolidone -5-carboxylic acid in Examples 1 to 8.

While particular embodiments of the invention have been described it will be understood of course that the invention is not limited thereto since many obvious modifications can be made and it is intended to include within this invention any such modifications as will fall within the scope of the appended claims.

Having now described the invention, we claim:

1. A method for topically administering systemically active agents through the skin or mucosal membranes of a human or animal which method comprises the topical administration of effective amounts of a systemically active agent and a membrane penetration enhancer having the structural formula

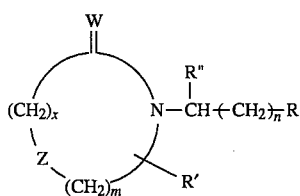

or the pharmaceutically acceptable salt thereof, wherein
W represents oxygen, sulfur or two hydrogen radicals;
Z represents —$CH_2$—;
R represents alkyl optionally substituted with one to three double or triple bonds, —SR''', —OR''', —NHR''', or —$COOR_1$;
R''' represents alkyl, alkylthioalkyl, alkoxyalkyl, aminoalkyl, optionally substituted with a phenyl, or benzoyl;
R' represents hydrogen, alkyl, alkoxy, acyloxy, alkylthio, hydroxy or —$(CH_2)_y COOR_1$;
R" represents hydrogen or —$(CH_2)_y COOR_1$;
$R_1$, in each instance, independently represents hydrogen or lower alkyl;
y, in each instance, is between zero and 3, inclusive;
m is between one and 4, inclusive;
n is between one and 24, inclusive; and
x is zero or one, inclusive;
with the provisos that when R" is hydrogen, then W is two hydrogen radicals and R' is not hydrogen; and when R' is hydrogen, then R" is not hydrogen.

2. The method in claim 1 wherein m is 2, 3 or 4; x is zero or 1; and n is between 5 and 12.

3. The method of claim 1 wherein the systemically active agent is a therapeutic agent.

4. The method of claim 3 wherein the administration is concurrent.

5. The method of claim 1 wherein the membrane penetration enhancer is selected from the group consisting of 2-dodecyl,2-N-(2-pyrrolidone)-acetic acid, 2-pentyl,2-N-(2-pyrrolidone)-acetic acid and 2-dodecyl,2-N-(azacycloheptane-2-one)acetic acid.

6. The method for claim 1 wherein the systemically active agent is selected from the group consisting of haloperidol, isosorbide dinitrate, nitroglycerin, estradiol, clonidine, propranolol, indomethacin, nifedipine, nicardipine, diclofenac and metaproterenol.

7. The method of claim 5 wherein the systemically active agent is selected from the group consisting of haloperidol, isosorbide dinitrate, nitroglycerin, estradiol, clonidine, propranolol, indomethacin, nifedipine, nicardipine, diclofenac and metaproterenol.

* * * * *